United States Patent
Wang et al.

(10) Patent No.: US 11,187,520 B2
(45) Date of Patent: Nov. 30, 2021

(54) OPTICAL COHERENCE TOMOGRAPHY DEVICE

(71) Applicant: SHENZHEN WINSTAR MEDICAL TECHNOLOGY COMPANY LIMITED, Shenzhen (CN)

(72) Inventors: Chichiu Wang, Hongkong (CN); Weijie Ming, Guangzhou (CN); Jun Gao, Guangzhou (CN); Yejing Li, Guangzhou (CN); Junqing He, Guangzhou (CN)

(*) Notice: Subject to any disclaimer, the term of this patent is extended or adjusted under 35 U.S.C. 154(b) by 0 days.

(21) Appl. No.: 17/280,914

(22) PCT Filed: Jul. 27, 2018

(86) PCT No.: PCT/CN2018/097345
§ 371 (c)(1),
(2) Date: Mar. 28, 2021

(87) PCT Pub. No.: WO2020/019281
PCT Pub. Date: Jan. 30, 2020

(65) Prior Publication Data
US 2021/0310790 A1    Oct. 7, 2021

(30) Foreign Application Priority Data
Jul. 23, 2018 (CN) .......................... 201810812476.3

(51) Int. Cl.
*A61B 5/05* (2021.01)
*G01B 9/02* (2006.01)
*G02B 6/36* (2006.01)
*A61B 5/00* (2006.01)

(52) U.S. Cl.
CPC ........ *G01B 9/02091* (2013.01); *A61B 5/0066* (2013.01); *A61B 5/0084* (2013.01); *G01B 9/02049* (2013.01); *G02B 6/3604* (2013.01); *A61B 2562/228* (2013.01)

(58) Field of Classification Search
None
See application file for complete search history.

(56) References Cited

FOREIGN PATENT DOCUMENTS

| CN | 104111586 A | 10/2014 |
|---|---|---|
| CN | 108095691 A | 6/2018 |
| EP | 2557441 A1 | 2/2013 |

*Primary Examiner* — Joel F Brutus
(74) *Attorney, Agent, or Firm* — Bayramoglu Law Offices LLC

(57) ABSTRACT

An optical coherence tomography device includes a base with a detection end and a mounting end, a movable base and a second drive mechanism. An optical imaging catheter is pivotally connected to the detection end. The optical imaging catheter is provided with an imaging end and a connecting end. The connecting end is detachably connected to the detection end, and the connecting end is provided with a first connecting part. The movable base is provided with a fiber optic rotary joint, a hollow shaft and a first drive mechanism. The end of the hollow shaft is provided with a second connecting part. When the movable base moves toward the detection end, the second connecting part is configured to be connected to the first connecting part so that the optical imaging catheter is coupled with the hollow shaft. The device is capable of manually or automatically connecting the optical imaging catheter.

10 Claims, 3 Drawing Sheets

OPTICAL COHERENCE TOMOGRAPHY DEVICE

CROSS REFERENCE TO THE RELATED APPLICATIONS

This application is the national phase entry of International Application No. PCT/CN2018/097345, filed on Jul. 27, 2018, which is based upon and claims priority to Chinese Patent Application No. 201810812476.3, filed on Jul. 23, 2018, the entire contents of which are incorporated herein by reference.

TECHNICAL FIELD

The present invention relates to an optical coherence tomography device.

BACKGROUND

Optical Coherence Tomography (OCT) is an optical imaging technique based on the principle of low-coherence interferometry, in which two- or three-dimension images of biological tissues are captured by detecting back-reflection or scattering signals of low-coherence light incident on different tissue types. OCT was first proposed by a research team from the Massachusetts Institute of Technology in 1991. Compared with traditional imaging techniques such as nuclear magnetic resonance, X-rays and ultrasound, OCT has a higher resolution, reaching up to the micron level, and also there is no risk of radiation since OCT devices typically operate in the near-infrared range. Thus, OCT is regarded as non-radiative computerized tomography (CT), but has a resolution that is 100 times higher than that of CT. Compared with optical confocal microscopy for in-vitro detection, OCT has a greater penetration depth and is thus capable of detecting micron-level morphological changes of biological tissues. Moreover, OCT systems are easy to miniaturize and make portable by virtue of optical fiber technology, and thus are capable of performing real-time detection on tissues of bodies. In recent years, OCT, as a new imaging technique, has advanced by leaps and bounds. Traditional OCT equipment is widely used in clinical diagnosis in the field of ophthalmology. Additionally, researchers are using OCT imaging methods in various applications such as skin, teeth, cardiovascular, esophagus and brain imaging in combination with optical fiber technology and endoscopy.

When OCT is used to detect a respiratory tract, a reproductive tract or other tubular organs, the main body of an OCT device transmits the optical signal to a fiber optic rotary joint, which transmits the optical signal. Then an optical imaging catheter is connected to a drive unit of the main body and an optical path of the fiber optic rotary joint. In this way, the drive unit drives the optical imaging catheter to perform a 360° rotation scan about the main axis thereof to obtain a B-scan image. When the exam is finished, the optical imaging catheter should be disassembled for cleaning and disinfection. It is highly desirable to provide a method to connect and remove the optical catheter from the drive unit conveniently.

SUMMARY

In order to overcome the shortcomings of the prior art, the objective of the present invention is to provide an optical coherence tomography device, which is capable of connecting and removing the optical catheter from the drive unit conveniently either manually or automatically.

The objective of the present invention is achieved by adopting the following technical solutions.

An optical coherence tomography device includes:

a base, wherein one end of the base is provided with a detection end, and the other end of the base is provided with a mounting end; an optical imaging catheter is pivotally connected to the detection end; the optical imaging catheter can move along the length direction of the base; the optical imaging catheter is provided with an imaging end and a connecting end, wherein the connecting end is detachably connected to the detection end, and the connecting end is provided with a first connecting part;

a movable base, wherein the movable base is mounted at the mounting end of the base and can move toward or away from the detection end along the length direction of the base; the movable base is provided with a fiber optic rotary joint configured to transmit optical signals, a hollow shaft and a first drive mechanism; the fiber optic rotary joint is set away from the detection end and is fixedly connected to the movable base; the end of the fiber optic rotary joint adjacent to the detection end extends into the hollow shaft; the hollow shaft is pivotally connected to the movable base, and the end of the hollow shaft adjacent to the detection end is provided with a second connecting part; when the movable base moves toward the detection end, the second connecting part is configured to be connected to the first connecting part so that the optical imaging catheter is coupled with the hollow shaft and the optical imaging catheter is connected to an optical path of the fiber optic rotary joint; the first drive mechanism is configured to drive the hollow shaft to rotate; and a second drive mechanism, wherein the second drive mechanism is configured to drive the movable base to move along the length direction of the base.

Further, a clamping member and a third drive mechanism are arranged on the movable base. The clamping member is arranged under the second connecting part. The third drive mechanism is configured to drive the clamping member to move toward or away from the second connecting part along the height direction of the base. When the first connecting part and the second connecting part are connected, the clamping member moves toward the second connecting part to tightly clamp the first connecting part and the second connecting part.

Further, the third drive mechanism includes a first linear motor. The housing of the first linear motor is fixedly connected to the movable base. The clamping member is fixedly connected to a power output end of the first linear motor.

Further, the detection end of the base is provided with a first trigger switch. The first trigger switch is configured to transmit a first trigger signal to the third drive mechanism after the clamping member tightly clamps the first connecting part and the second connecting part.

Further, the first drive mechanism includes a synchronous motor, a synchronous belt and two synchronous wheels. The housing of the synchronous motor is fixedly connected to the movable base, and a rotating shaft of the synchronous motor is fixedly connected to one of the synchronous wheels. The other synchronous wheel is sleeved on the outside of the hollow shaft and fixedly connected to the hollow shaft. The two ends of the synchronous belt are synchronously wound around the two synchronous wheels.

Further, the second drive mechanism includes a leadscrew motor, a leadscrew, a nut, and a guide mechanism. The housing of the leadscrew motor is fixedly connected to the base. The leadscrew extends along the length direction of the base and is synchronously connected to a rotor of the leadscrew motor. The nut is sleeved on the outside of the leadscrew and is in a thread-fit with the leadscrew. The nut is fixedly connected to the bottom end of the movable base, and is guided by the guide mechanism to move along the direction in which the leadscrew extends.

Further, the detection end of the base is provided with a stop block and a fourth drive mechanism. The stop block is movably mounted at the detection end. The fourth drive mechanism is configured to drive the stop block to move toward or away from the connecting end. The stop block is configured to block the end surface of the connecting end after moving toward the connecting end.

Further, the fourth drive mechanism includes a second linear motor. The housing of the second linear motor is fixedly connected to the base. The stop block is fixedly connected to a power output end of the second linear motor.

Further, the detection end of the base is provided with a second trigger switch. The second trigger switch is configured to transmit a second trigger signal to the fourth drive mechanism when the stop block blocks the end surface of the connecting end.

Further, a third trigger switch is arranged on the hollow shaft. The third trigger switch is configured to transmit a third trigger signal to the first drive mechanism after the hollow shaft rotates an angle A.

Compared with the prior art, the present invention has the following advantages. The movable base moves toward the detection end to connect the second connecting part of the hollow shaft on the movable base to the first connecting part of the optical imaging catheter, so that the optical imaging catheter is synchronously coupled with the hollow shaft. Moreover, the optical imaging catheter is either manually or automatically connected to or disconnected from the optical path of the optical fiber of the fiber optic rotary joint on the movable base very conveniently. After that, the hollow shaft is driven to rotate by the first drive mechanism to drive the optical imaging catheter to rotate to capture an image of a single section of a lumen. On the other hand, the second drive mechanism drives the movable base to reciprocate to drive the optical imaging catheter to reciprocate, so that the optical imaging catheter is capable of scanning the whole section of the lumen to capture a stereoscopic 3D image.

In the figures: 10, base; 11, fourth trigger switch; 20, movable base; 30, fiber optic rotary joint; 40, optical imaging catheter; 41, connecting end; 411, first connecting part; 50, hollow shaft; 51, second connecting part; 60, first linear motor; 61, clamping member; 62, first trigger switch; 70, second linear motor; 71, stop block; 72, second trigger switch; 80, synchronous motor; 81, synchronous wheel; and 82, third trigger switch.

DETAILED DESCRIPTION OF THE EMBODIMENTS

Hereinafter, the present invention will be further described with reference to the drawings and specific implementations. It should be noted that, in case of no conflict, the various embodiments or various technical features described below can be arbitrarily combined to form a new embodiment.

Figure 1:
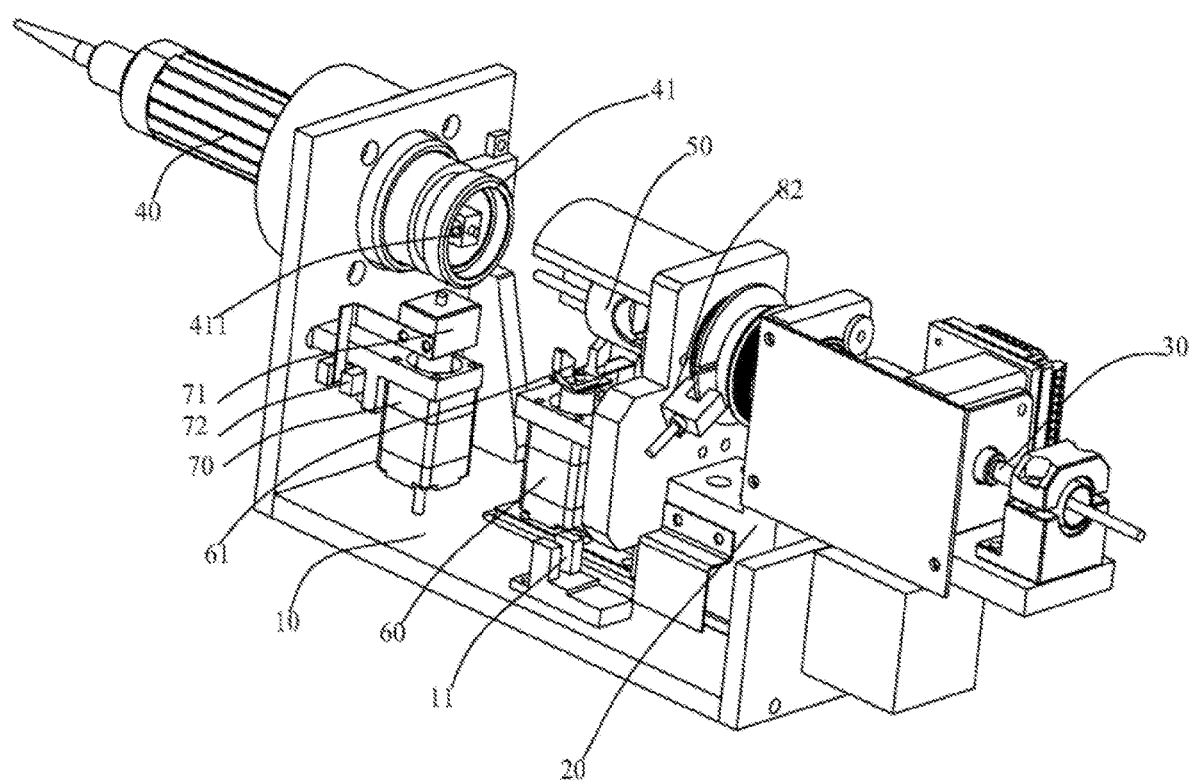
FIG. 1 is a schematic diagram of the structure of the present invention.
Figure 2:
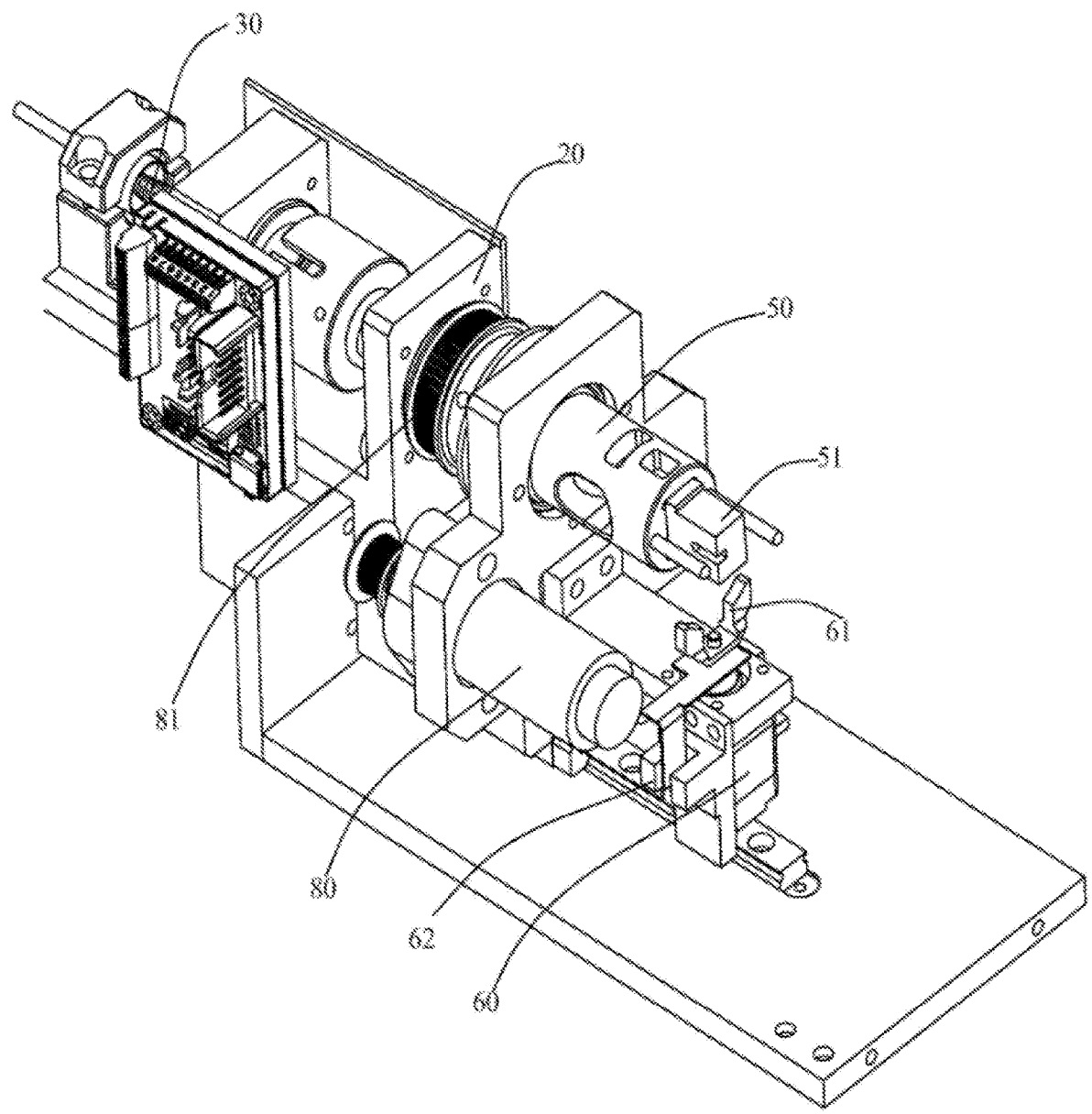
FIG. 2 is a schematic diagram of the structure of the mounting end on the base of the present invention.
Figure 3:
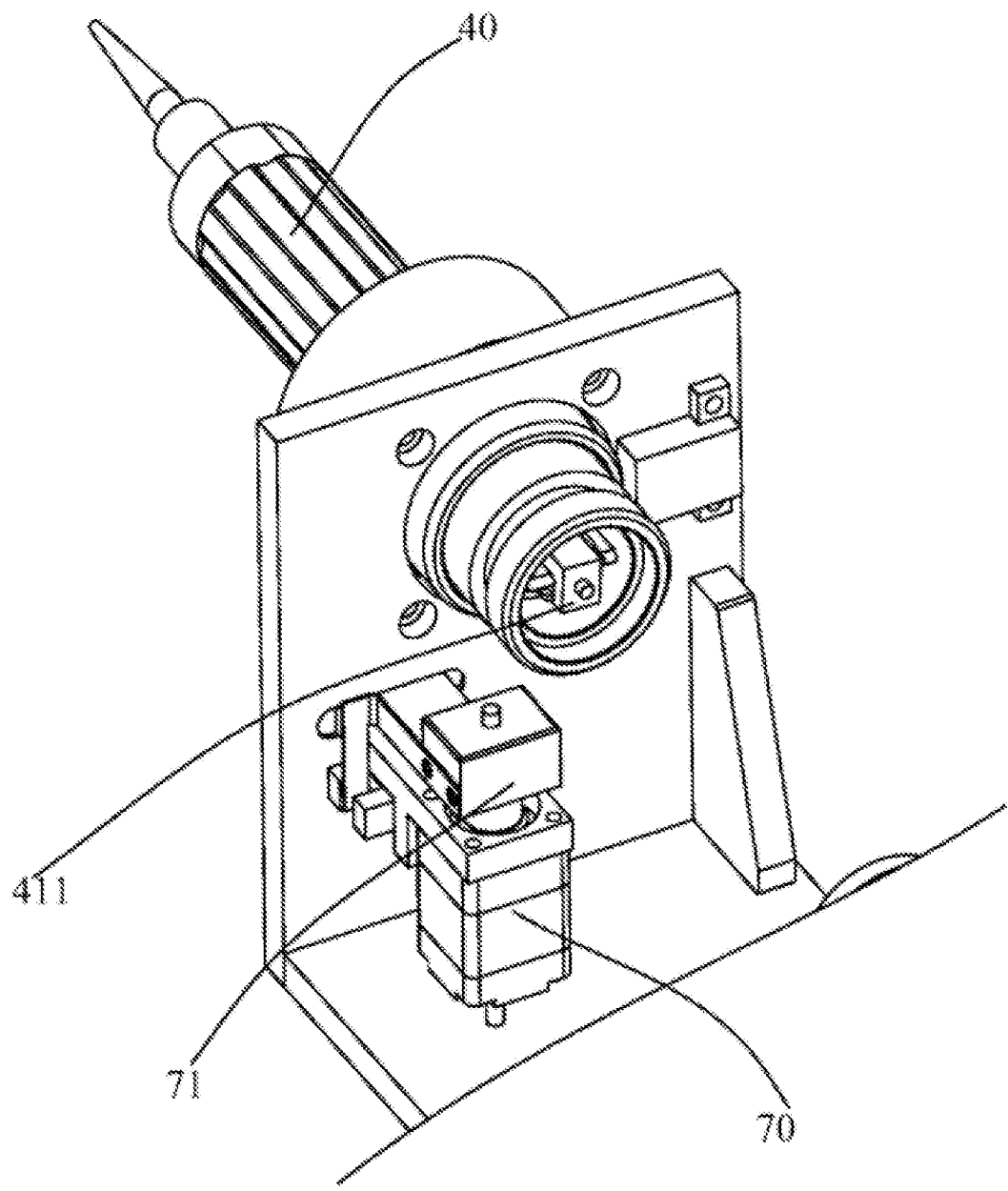
FIG. 3 is a schematic diagram of the structure of the detection end on the base of the present invention.

As shown in FIGS. 1, 2 and 3, an optical coherence tomography device includes the base 10, the movable base 20, and a second drive mechanism. One end of the base 10 is provided with a detection end, and the other end of the base 10 is provided with a mounting end. The optical imaging catheter 40 is pivotally connected to the detection end, and the optical imaging catheter 40 can move along the length direction of the base 10. Specifically, the optical imaging catheter 40 is provided with an imaging end and the connecting end 41. The connecting end 41 is detachably connected to the detection end, and the connecting end 41 is provided with the first connecting part 411.

In addition, the movable base 20 is mounted at the mounting end and can move toward or away from the detection end along the length direction of the base 10. The movable base 20 is provided with the fiber optic rotary joint 30, the hollow shaft 50 and a first drive mechanism. The fiber optic rotary joint 30 is configured to transmit optical signals. The fiber optic rotary joint 30 is set away from the detection end and is fixedly connected to the movable base 20, and the end of the fiber optic rotary joint 30 adjacent to the detection end extends into the hollow shaft 50. The hollow shaft 50 is pivotally connected to the movable base 20. The first drive mechanism is configured to drive the hollow shaft 50 to rotate. The end of the hollow shaft 50 adjacent to the detection end is provided with the second connecting part 51. When the movable base 20 moves toward the detection end, the second connecting part 51 is configured to be connected to the first connecting part 411, so that the optical imaging catheter 40 is coupled with the hollow shaft 50 to connect the optical imaging catheter 40 to an optical path of the fiber optic rotary joint 30. Specifically, the movable base 20 is driven by the second drive mechanism to move along the length direction of the base 10.

On the basis of the above structure, when the optical coherence tomography device is in use, the second drive mechanism drives the movable base 20 to move toward the detection end to connect the second connecting part 51 of the hollow shaft 50 on the movable base 20 to the first connecting part 411 of the optical imaging catheter 40, so that the optical imaging catheter 40 is synchronously coupled with the hollow shaft 50, and the optical imaging catheter 40 is automatically or manually connected to or disconnected from the optical path of the optical fiber of the fiber optic rotary joint 30 on the movable base 20. The imaging end of the connected optical imaging catheter 40 is applied to the inside of a lumen for detection. The main body of the device is turned on to transmit an optical signal to the fiber optic rotary joint 30, and the optical signal is transmitted to the optical imaging catheter 40 through the fiber optic rotary joint 30. After that, the hollow shaft 50 is driven to rotate by the first drive mechanism, thereby driving the optical imaging catheter 40 to rotate, so that the optical imaging catheter 40 is capable of capturing an image of a single section of the lumen. On the other hand, the second drive mechanism drives the movable base 20 to reciprocate, thereby driving the optical imaging catheter 40 to reciprocate, so that the optical imaging catheter 40 is capable of scanning the whole section of the lumen to capture a stereoscopic 3D image.

It should be noted that the fiber optic rotary joint 30, the hollow shaft 50 and the optical imaging catheter 40 are coaxially connected on the base 10 in the following manner. The movable base 20 is provided with two mounting holes that are coaxially formed, in which the fiber optic rotary joint 30 and the hollow shaft 50 are mounted. Also, the detection end of the base 10 is provided with a mounting hole in which the optical imaging catheter 40 is mounted, and the mounting hole is coaxial with the two mounting holes to facilitate automatic connection.

In addition, the first connecting part 411 can be implemented by using a known connecting male terminal of an optical fiber connector in the prior art, while the second connecting part 51 can be implemented by using a known connecting female terminal of the optical fiber connector in the prior art. After the movable base 20 moves toward the optical imaging catheter 40 that is adjacent to the detection end, the connecting male terminal of the optical fiber connector is plugged into the connecting female terminal of the optical fiber connector to connect the optical path.

Further, in the present embodiment, the clamping member 61 and a third drive mechanism are arranged on the movable base 20. Specifically, the clamping member 61 is arranged under the second connecting part 51. The third drive mechanism is configured to drive the clamping member 61 to move toward or away from the second connecting part 51 along the height direction of the base 10, that is, to drive the clamping member 61 to move up and down. When the first connecting part 411 and the second connecting part 51 are connected, the clamping member 61 moves toward the second connecting part 51 to tightly clamp the first connecting part 411 and the second connecting part 51. In other words, after the movable base 20 moves toward the detection end, the first connecting part 411 has been connected to the second connecting part 51, and the third drive mechanism drives the clamping member 61 to move toward the second connecting part 51, so that the clamping member 61 securely clamps the connection portion between the first connecting part 411 and the second connecting part 51 to reinforce the connection structure thereof. When the first connecting part 411 and the second connecting part 51 needs to be disconnected, the clamping member 61 is driven to move downward by the third drive mechanism. Specifically, the clamping member 61 can be implemented by using a structure such as a clamping jaw in the prior art.

Further, the third drive mechanism includes the first linear motor 60. The housing of the first linear motor 60 is fixedly connected to the movable base 20. The clamping member 61 is fixedly connected to the power output end of the first linear motor 60, that is, the first linear motor 60 can drive the clamping member 61 to move up and down. The third drive mechanism has a simple driving structure and is convenient to use. Optionally, the third drive mechanism can also be implemented by other linear motion output mechanisms such as a drive cylinder and a leadscrew transmission mechanism in the prior art.

Further, the detection end of the base 10 is provided with a first trigger switch. The first trigger switch is configured to transmit a first trigger signal to the third drive mechanism after the clamping member 61 tightly clamps the first connecting part 411 and the second connecting part 51. That is, after the clamping member 61 tightly clamps the first connecting part 411 and the second connecting part 51, the first trigger switch 62 is triggered to control the third drive mechanism to stop in time. In the present embodiment, the first trigger switch 62 is a grating sensor, and the clamping member 61 is provided with an optical path blocking plate. The clamping member 61 moves up and down, so that the optical path blocking plate can disconnect or connect the optical path of the grating sensor to control the third drive mechanism to start or stop. Optionally, the first trigger switch can also be a contact switch in the prior art.

Further, the first drive mechanism includes the synchronous motor 80, a synchronous belt and two synchronous wheels 81. The housing of the synchronous motor 80 is fixedly connected to the movable base 20, and a rotating shaft of the synchronous motor 80 is fixedly connected to one of the synchronous wheels 81. The other synchronous wheel 81 is sleeved on the outside of the hollow shaft 50 and fixedly connected to the hollow shaft 50. The two ends of the synchronous belt are synchronously wound around the two synchronous wheels 81. When the hollow shaft 50 is driven to rotate, the synchronous motor 80 is started to rotate to drive one of the synchronous wheels 81 to rotate, and the other synchronous wheel 81 fixedly connected to the hollow shaft 50 is also rotated through the transmission of the synchronous belt, so as to drive the hollow shaft 50 to rotate. In this way, the transmission structure is simple and stable. Optionally, the first drive mechanism can also be directly implemented by an electric motor, or implemented by a combination of an electric motor and a gear transmission structure.

Further, the second drive mechanism specifically includes a leadscrew motor, a leadscrew, a nut, and a guide mechanism. The housing of the leadscrew motor is fixedly connected to the base 10. The leadscrew extends along the length direction of the base 10 and is synchronously connected to a rotor of the leadscrew motor. The nut is sleeved on the outside of the leadscrew and is in a thread-fit with the leadscrew. The nut is fixedly connected to the bottom end of the movable base 20, and is guided by the guide mechanism to move along the direction in which the leadscrew extends. When the movable base 20 is driven to move along the length direction of the base 10, the leadscrew motor is started to rotate to drive the leadscrew to rotate, and the rotation of the leadscrew is transformed into a linear motion along the direction in which the leadscrew extends (that is, the length direction of the base 10) through the nut that is in a thread-fit with the leadscrew and the guidance of the guide mechanism, so as to drive the movable base 20 fixedly connected to the nut to move along the length direction of the base 10. The guide mechanism specifically includes a sliding rail fixedly connected to the base 10 and a sliding groove formed at the bottom end of the movable base 20, and the sliding rail is slidably embedded in the sliding groove.

Optionally, the fourth trigger switch 11 can be arranged on the base 10. The fourth trigger switch 11 is configured to transmit a signal to the second drive mechanism to control the movable base 20 to start or stop in time when the movable base 20 moves to the two ends of the base 10. The fourth trigger switch 11 can also adopt a grating sensor. An optical path blocking plate is arranged on the movable base 20. The movable base 20 moves back and forth until the optical path blocking plate is disconnected or connected to the optical path of the grating sensor to control the second drive mechanism to start or stop. Optionally, the fourth trigger switch 11 can also be a contact switch in the prior art.

Further, the detection end of the base 10 is provided with the stop block 71 and a fourth drive mechanism. The stop block 71 is movably mounted at the detection end. The fourth drive mechanism is configured to drive the stop block 71 to move toward or away from the connecting end 41. The stop block 71 is configured to block the end surface of the connecting end 41 after moving toward the connecting end 41. In this way, when the first connecting part 411 needs to be disconnected from the second connecting part 51, the stop block 71 is driven to move upward by the fourth drive mechanism to block the end surface of the connecting end 41 of the optical imaging catheter 40, so that the movable base 20 moves away from the optical imaging catheter 40, and the movement of the optical imaging catheter 40 is stopped by the stop block 71, so that the second connecting part 51 is separate and disconnected from the first connecting part 411. Optionally, without the stop block 71 and the fourth drive mechanism, the first connecting part 411 is separate from the second connecting part 51 manually.

Further, the fourth drive mechanism includes the second linear motor 70. The housing of the second linear motor 70 is fixedly connected to the base 10. The stop block 71 is fixedly connected to the power output end of the second linear motor 70. That is, the stop block 71 is driven by the second linear motor 70 to move up and down. The driving structure is simple and convenient to use. Optionally, the fourth drive mechanism can also be implemented by other linear motion output mechanisms such as a drive cylinder and a leadscrew drive mechanism in the prior art.

Specifically, the detection end of the base 10 is provided with the second trigger switch 72. The second trigger switch 72 is configured to transmit a second trigger signal to the fourth drive mechanism when the stop block 71 blocks the end surface of the connecting end 41. That is, when the stop block 71 moves to the end surface of the connecting end 41, the second trigger switch 72 is triggered to control the fourth drive mechanism to stop in time. In the present embodiment, the second trigger switch 72 can also adopt a grating sensor, and an optical path blocking plate is arranged on the stop block 71. When the stop block 71 moves up and down, the optical path blocking plate can disconnect or connect the optical path of the grating sensor to control the fourth drive mechanism to start or stop. Optionally, the second trigger switch 72 can also be a contact switch in the prior art.

Optionally, the third trigger switch 82 is arranged on the hollow shaft 50, and the third trigger switch 82 is configured to transmit a third trigger signal to the first drive mechanism after the hollow shaft 50 rotates an angle A. In the present embodiment, the third trigger switch 82 adopts a grating sensor, and an optical path blocking plate is sleeved on the hollow shaft 50. A notch is provided on the optical path blocking plate, and the position of the notch located in the optical path of the grating sensor (that is, the optical path is connected) serves as a zero position. The first drive mechanism is controlled to start, that is, the hollow shaft 50 starts to rotate at a position as the starting point for recording the 360° scan performed by the optical imaging catheter 40. After the hollow shaft 50 rotates an angle A (the hollow shaft 50 rotates 360° in the present embodiment), the notch of the optical path blocking plate returns to the zero position, which is counted as the first 360° scan of the optical imaging catheter 40 at this time. Similarly, the third trigger switch 82 can also be implemented by a contact switch in the prior art.

The foregoing embodiments are only preferred embodiments of the present invention, and cannot be construed to limit the scope of protection of the present invention. Any non-substantive changes and substitutions made by those skilled in the art on the basis of the present invention belong to the scope of protection claimed by the present invention.

What is claimed is:

1. An optical coherence tomography device, comprising:
    a base,
    a movable base, and
    a second drive mechanism;
    wherein
    a first end of the base is provided with a detection end, and a second end of the base is provided with a mounting end;
    an optical imaging catheter is pivotally connected to the detection end;
    the optical imaging catheter moves along a length direction of the base;
    the optical imaging catheter is provided with an imaging end and a connecting end, wherein the connecting end is detachably connected to the detection end, and the connecting end is provided with a first connecting part;
    the movable base is mounted at the mounting end and the movable base moves toward or away from the detection end along the length direction of the base;
    the movable base is provided with a fiber optic rotary joint configured to transmit optical signals, a hollow shaft and a first drive mechanism;
    the fiber optic rotary joint is set away from the detection end, and the fiber optic rotary joint is fixedly connected to the movable base;
    an end of the fiber optic rotary joint is adjacent to the detection end, and the end of the fiber optic rotary joint extends into the hollow shaft;
    the hollow shaft is pivotally connected to the movable base, and an end of the hollow shaft adjacent to the detection end is provided with a second connecting part;
    when the movable base moves toward the detection end, the second connecting part is configured to be connected to the first connecting part, and the optical imaging catheter is coupled with the hollow shaft to connect the optical imaging catheter to an optical path of the fiber optic rotary joint;
    the first drive mechanism is configured to drive the hollow shaft to rotate; and
    the second drive mechanism is configured to drive the movable base to move along the length direction of the base.

2. The optical coherence tomography device according to claim 1, wherein
    a clamping member and a third drive mechanism are arranged on the movable base, and the clamping member is arranged under the second connecting part;
    the third drive mechanism is configured to drive the clamping member to move toward or away from the second connecting part along a height direction of the base; and
    when the first connecting part and the second connecting part are connected, the clamping member moves toward the second connecting part to tightly clamp the first connecting part and the second connecting part.

3. The optical coherence tomography device according to claim 2, wherein
    the third drive mechanism comprises a first linear motor, and a housing of the first linear motor is fixedly connected to the movable base; and
    the clamping member is fixedly connected to a power output end of the first linear motor.

4. The optical coherence tomography device according to claim 2, wherein
    the detection end of the base is provided with a first trigger switch, and the first trigger switch is configured to transmit a first trigger signal to the third drive mechanism after the clamping member tightly clamps the first connecting part and the second connecting part.

5. The optical coherence tomography device according to claim 1, wherein the first drive mechanism comprises a synchronous motor, a synchronous belt and two synchronous wheels;

a housing of the synchronous motor is fixedly connected to the movable base;

a rotating shaft of the synchronous motor is fixedly connected to a first synchronous wheel of the two synchronous wheels, and a second synchronous wheel of the two synchronous wheels is sleeved on an outside of the hollow shaft and the second synchronous wheel is fixedly connected to the hollow shaft; and two ends of the synchronous belt are synchronously wound around the two synchronous wheels.

6. The optical coherence tomography device according to claim 1, wherein the second drive mechanism comprises a leadscrew motor, a leadscrew, a nut, and a guide mechanism;

a housing of the leadscrew motor is fixedly connected to the base;

the leadscrew extends along the length direction of the base and the leadscrew is synchronously connected to a rotation shaft of the leadscrew motor;

the nut is sleeved on an outside of the leadscrew and the nut is in a thread-fit with the leadscrew;

the nut is fixedly connected to a bottom end of the movable base, and the nut is guided by the guide mechanism to move along the length direction of the base.

7. The optical coherence tomography device according to claim 1, wherein the detection end of the base is provided with a stop block and a fourth drive mechanism, and the stop block is movably mounted at the detection end;

the fourth drive mechanism is configured to drive the stop block to move toward or away from the connecting end; and the stop block is configured to block an end surface of the connecting end after moving toward the connecting end.

8. The optical coherence tomography device according to claim 7, wherein the fourth drive mechanism comprises a second linear motor, and a housing of the second linear motor is fixedly connected to the base; and the stop block is fixedly connected to a power output end of the second linear motor.

9. The optical coherence tomography device according to claim 7, wherein the detection end of the base is provided with a second trigger switch, and the second trigger switch is configured to transmit a second trigger signal to the fourth drive mechanism when the stop block blocks the end surface of the connecting end.

10. The optical coherence tomography device according to claim 1, wherein a third trigger switch is arranged on the hollow shaft, and the third trigger switch is configured to transmit a third trigger signal to the first drive mechanism after the hollow shaft rotates an angle A.

* * * * *